(12) United States Patent
Reich et al.

(10) Patent No.: US 6,828,800 B2
(45) Date of Patent: Dec. 7, 2004

(54) SINGLE-MOLECULE DETECTOR (75) Inventors: Ziv Reich, Yohanan (IL); Dan Shahar, Savyon (IL); Ruti Kapon, Ramat Gan (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 72 days.

(21) Appl. No.: 10/013,845

(22) Filed: Dec. 13, 2001

(65) Prior Publication Data

US 2002/0118005 A1 Aug. 29, 2002

Related U.S. Application Data (60) Provisional application No. 60/255,138, filed on Dec. 14, 2000.

(51) Int. Cl.⁷ .............................................. G01R 27/26
(52) U.S. Cl. ..................... 324/658; 324/660; 324/661
(58) Field of Search ................................ 324/658, 660, 324/661, 71.3, 71.1, 464; 434/6

(56) References Cited

U.S. PATENT DOCUMENTS 5,922,537 A * 7/1999 Ewart et al. .................... 435/6
6,323,660 B1 * 11/2001 Kunc et al. ................. 324/661
6,633,172 B1 * 10/2003 Doemens et al. ........... 324/661

* cited by examiner

*Primary Examiner*—Anjan Deb
*Assistant Examiner*—Walter Benson
(74) *Attorney, Agent, or Firm*—G. E. Ehrlich (1995) Ltd.

(57) ABSTRACT

A detector, for determining presence, number, length concentration, position and/or motion of at least one particle present in a fluid and having a dielectric coefficient other than a dielectric coefficient of the fluid, the detector including: (a) a capacitor, comprising a first conductive plate and a second conductive plate defining an inter-plate volume having a longitudinal axis; and (b) at least two electrical contacts, connecting each of the first and second conductive plates to a capacitance measuring device; the capacitor being characterized by at least one variable parameter so as to allow determination and/or monitoring of presence, number, length concentration, position and/or at least one motion characteristic of the at least one particle placed within the inter-plate volume of the capacitor.

54 Claims, 5 Drawing Sheets

SINGLE-MOLECULE DETECTOR

This application claims the benefit of priority from U.S. Provisional Patent application No. 60/255,138, filed Dec. 14, 2000.

FIELD AND BACKGROUND OF THE INVENTION

The present invention relates to single molecule detectors, methods of manufacturing same and methods of detecting single molecules using same. More particularly, the present invention relates to detectors suited for detecting the presence, motion and/or length of one or more molecules, methods of manufacturing same and methods of detecting the presence, motion and/or length of one or more molecules at a resolution, as high as, a nanometer resolution.

Single-molecule experimental techniques provide fascinating possibilities for studying systems in which molecular individuality matters. This is particularly true when the molecule forms a part of a complex environment which substantially affects its behavior, or when the molecule itself has an intricate internal structure resulting in a complex energy landscape. Because single-molecule experiments offer unique information on macromolecular interactions and chemical dynamics, unattainable by ensemble-averaged measurements, such experiments have had a remarkable impact on many scientific and technological disciplines. Single molecule studies on biological systems have already yielded important information relevant to problems that involve macromolecular motion and confirmational dynamics, photo biology, protein folding and enzyme mechanics. Undoubtedly, single-molecule studies will remain central to the biological sciences in years to come.

Single-molecule studies, as oppose to ensemble-based experiments, refer to a class of measurements where the behavior of individual molecules is followed. One advantage of such studies is the ability to determine the distribution of molecular properties by conducting many sequential measurements, hence affording the investigation of inhomogeneous systems. Another advantage of single-molecule studies is that single-molecule trajectories are direct records of the system's fluctuations, and as such they provide dynamical and statistical information that is hidden in ensemble-averaged results. In addition, single-molecule measurements permit real-time observation of rarely populated transients, which are otherwise difficult or impossible to capture using conventional methods.

Several basic experimental approaches and their derivatives, which allow for single-molecule experiments, are known in the art. These include scanning force microscopy (SFM), optical trapping and optical microscopy and spectroscopy. SFM and optical trapping require that an external, time-varying load be applied to the substrate to enable measurement. Although SFM may be used as an imaging tool, its functionality as such is slow. Furthermore, when used as a force sensor, SFM can reliably probe motions only parallel to the scanning tip, whereas other motions cannot be detected effectively. In addition, when used as a characterization tool, SFM has a low throughput and requires highly trained personal.

Optical techniques are comparatively fast allowing the recording of molecular trajectories down to the 10–100 millisecond time-scales, and can achieve center-position accuracy of a few nanometers.

One optical technique of single molecule detection is based on flow cytometry, where an analyte solution is delivered into a rapidly flowing sheath fluid and hydrodynamically focused into a narrow sample stream. Another approach is based on analyte movement through a capillary. In flow cytometry, a sample stream passes through the center of a probe volume defined by the diameter of the focused excitation laser beam and a spatial filter placed in the image plane of a light collecting objective. Single fluorescent molecules are detected by the bursts of photons emitted as they flow through the detection volume one-at-a-time. However, focused laser beams, can generate a notable trapping potential for sizable molecules, which may affect the accuracy of the measurements. More important since these techniques rely heavily on fluorescence, they are prone to a number of photoinduced artifacts, such as triplet trapping and photobleaching. The latter dictates that observation times have to be short. Furthermore, extracting data from fluorescent and optical trapping techniques often requires complex image analysis.

Electrostatic, or capacitive, sensing is one of the most important and oldest precision sensing mechanisms. Macroscopic capacitive sensors and transducers of many shapes have been implemented. They are used for liquid level sensing, touch sensing, key switches, light switches and proximity detection.

Electret microphones implemented in telephones and tape recorders use capacitive sensing, as do Silicone accelerometers that deploy the air bag in a car. A key feature of capacitive sensors is their ability to detect the presence of material at a distance through variation in the dielectric constant. Some of the advantages of capacitive sensors are their sensitivity, accuracy and temperature stability. Furthermore, capacitive sensors are less noisy than resistive sensors and consume very little power.

On the microscopic level, the use of capacitive sensors is increasing rapidly. Use of microscopic level capacitive sensing are known in the art, for example Sohn, L. L., Saleh, O. A., Facer, G. R., Beavis, A. J., Allan, R. S. and Notterman, D. A., PNAS 97, 10687–10690 (2000), disclosed a devise intended to measure dielectric constant using a parallel plate capacitor. However, the device disclosed by Sohn et. al. fails to have any sensitivity to position. In addition, the resolution of this device is limited by the physical size of the device, hence it lacks the capability of a single molecule detection.

Capacitive sensors capable of single molecule detection have not yet been described in the art.

There is thus a widely recognized need for, and it would be highly advantageous to have, a single molecule detector and a method of detecting a single molecule, based on capacitive sensing.

SUMMARY OF THE INVENTION

According to one aspect of the present invention there is provided a detector, for determining presence, number, length concentration, position and/or motion of at least one particle present in a fluid and having a dielectric coefficient other than a dielectric coefficient of the fluid, the detector comprising: (a) a capacitor, comprising a first conductive plate and a second conductive plate defining an inter-plate volume having a longitudinal axis; and (b) at least two electrical contacts, connecting each of the first and second conductive plates to a capacitance measuring device; the capacitor being characterized by at least one variable parameter so as to allow determination and/or monitoring of presence, number, length concentration, position and/or at least one motion characteristic of the at least one particle placed within the inter-plate volume of the capacitor.

According to another aspect of the present invention there is provided A motion detection method comprising placing at least one particle present in a fluid and having a dielectric coefficient other than a dielectric coefficient of the fluid, within an inter-plate volume of a capacitor, being characterized by at least one variable parameter, and determining and/or monitoring presence, number, length concentration, longitudinal position and/or at least one motion characteristic of the at least one conductive particle, by determining a change in capacitance of the capacitor.

According to yet another aspect of the present invention there is provided a particle presence, number, length or concentration detector comprising; (a) a capacitor, comprising a first conductive plate and a second conductive plate substantially parallel to the first conductive plate, the first and second conductive plates defining an interplate volume having a longitudinal axis; and (b) at least two electrical contacts, connecting each of the first and second conductive plates to a capacitance measuring device; the capacitor being designed and constructed for allowing a determination of a presence, number or concentration of particles placed within the inter-plate volume of the capacitor, the particles being present in a fluid and having a dielectric coefficient other than a dielectric coefficient of said fluid.

According to still another aspect of the present invention there is provided a method of determining the presence, number, length or concentration of particles present in a fluid and having a dielectric coefficient other than a dielectric coefficient of the fluid, the method comprising placing the conductive particles in an inter-plate volume of a parallel plates capacitor and determining the presence, number, length or concentration of the conductive particles by determining a change in capacitance of the parallel plates capacitor.

According to still an additional aspect of the present invention there is provided a detector for determining presence, number, length concentration, position and/or motion of at least one particle present in a fluid and having a dielectric coefficient other than a dielectric coefficient of the fluid, the detector comprising: (a) a variable-width capacitor, comprising a first conductive plate and a second conductive plate having a variable distance therebetween and defining an inter-plate volume of a variable-width having a longitudinal axis; and (b) at least two electrical contacts, connecting each of the first and second conductive plates to a capacitance measuring device; the variable-width capacitor being designed and constructed for determination of a longitudinal position and/or monitoring a change of position along the longitudinal axis of a single conductive particle placed within the inter-plate volume of the variable-width capacitor.

According to a further aspect of the present invention there is provided a motion detection method comprising placing at least one particle present in a fluid and having a dielectric coefficient other than a dielectric coefficient of the fluid, within an inter-plate volume of a variable-width capacitor and determining and/or monitoring a longitudinal position and/or at least one motion characteristic of the at least one conductive particle by determining a change in capacitance of the variable-width capacitor.

According to further features in preferred embodiments of the invention described below, the at least one variable parameter is selected from the group consisting of a variable dielectric coefficient and a variable cross-sectional area, the cross-sectional area being perpendicular to the longitudinal axis.

According to still further features in the described preferred embodiments the at least one, particle is self-conductive.

According to still further features in the described preferred embodiments the at least one particle is linkable to at least one conductive particle.

According to still further features in the described preferred embodiments the at least one particle is selected from the group consisting of a cell, a bacterium, a biological molecule, an organic molecule and a polymer.

According to still further features in the described preferred embodiments the determination and/or monitoring is at a nanometer resolution.

According to still further features in the described preferred embodiments the determination and/or monitoring is in a sub-microsecond time scales.

According to still further features in the described preferred embodiments the first and second conductive plates engage opposite inner-faces of a capillary.

According to still further features in the described preferred embodiments the first and second conductive plates engage opposite outer-faces of a capillary.

According to still further features in the described preferred embodiments the capillary has a profile selected from the group consisting of a polygonal profile a circular profile an ellipsoidal profile and an irregular pattern profile.

According to still further features in the described preferred embodiments the capillary is characterized by a variable cross section at any position along the longitudinal axis.

According to still further features in the described preferred embodiments the at least one motion characteristic is selected from the group consisting of velocity and acceleration.

According to still further features in the described preferred embodiments the detector further comprising at least one additional conductive layer interposed between the first and the second conductive layers, the at least one additional conductive layer having a surface area substantially smaller than a surface area of both the first and the second conductive layers.

According to still further features in the described preferred embodiments the detector further comprising at least one electrical isolating layer, covering the at least one additional conductive layer.

According to still further features in the described preferred embodiments at least one additional conductive layer is grounded.

According to still further features in the described preferred embodiments the at least one additional conductive layer is a made of Gold.

According to still further features in the described preferred embodiments the electrical isolating layer is a made of quartz.

According to still further features in the described preferred embodiments the method further comprising providing a dielectric material between the first conductive plate and the second conductive plate, the dielectric material having a dielectric coefficient.

According to still further features in the described preferred embodiments the dielectric coefficient is constant.

According to still further features in the described preferred embodiments the dielectric coefficient varies along the longitudinal axis.

According to still further features in the described preferred embodiments a transverse dimension of the first and the second conductive plates, with respect to the longitudinal axis, is constant along the longitudinal axis.

According to still further features in the described preferred embodiments a transverse dimension of the first and the second conductive plates, with respect to the longitudinal axis, varies along the longitudinal axis.

According to still further features in the described preferred embodiments the step of positioning the first conductive plate and the second conductive plate comprises: (a) providing a pullable tube having a profile; (b) pulling the tube at a controlled rate so as to provide a capillary having a predetermined maximal diameter; and (c) applying the first and the second conductive plates on opposite faces of the capillary.

According to still further features in the tie described preferred embodiments the opposite faces are selected from the group consisting of opposite inner-faces and opposite outer-faces.

According to still further features in the described preferred embodiments the step of applying is effected from a procedure selected from the group consisting of evaporation, lift-off, shadow-evaporation, nano-manipulation and focused ion milling.

According to still further features in the described preferred embodiments the profile is selected from the group consisting of a polygonal profile a circular profile an ellipsoidal profile and an irregular pattern profile.

According to still further features in the described preferred embodiments the step of pulling the tube substantially retain the profile.

According to still further features in the described preferred embodiments the step of pulling the tube is done by a micropipette puller.

According to still further features in the described preferred embodiments the micropipette puller is a laser based micropipette puller.

According to still further features in the described preferred embodiments the laser is a $CO_2$ laser.

According to still further features in the described preferred embodiments the method further comprising the step of varying a diameter of the profile along the longitudinal axis, during or subsequent to the step of pulling the tube.

According to still further features in the described preferred embodiments the method further comprising the steps of applying at least one additional conductive layer onto the capillary, and covering the at least one additional conductive layer by an electrical isolating layer, prior to the step (c).

According to still further features in the described preferred embodiments the method further comprising grounding the at least one additional conductive layer.

According to still further features in the described preferred embodiments the at least one additional conductive layer is a made of a material selected from the group consisting of Gold and Aluminium.

According to still further features in the described preferred embodiments the covering is effected from a procedure selected from the group consisting of evaporation, lift-off, shadow-evaporation, nano-manipulation and focused ion milling.

According to still further features in the described preferred embodiments the nano-manipulation is done by atomic force microscope.

According to an additional aspect of the present invention there is provided a method of manufacturing a motion detector for detecting at least one conductive particle, the method comprising the steps of: positioning a first conductive plate and a second conductive plate such that the second conductive plate is spaced apart from the first conductive plate, so as to define an inter-plate volume having a longitudinal axis; and providing a at least two electrical contacts, connecting each of the first and the second conductive plates to a capacitance measuring device.

According to yet an additional aspect of the present invention there is provided a method of manufacturing a motion detector for detecting at least one conductive particle, the method comprising the steps of: (a) etching a non conductive substrate so as to provide at least two channels; (b) coating the at least two channels by a conductive material so as to provide at least two coated channels; and (d) providing a at least two electrical contacts, connecting each of the first and the second conductive plates to a capacitance measuring device.

According to further features in preferred embodiments of the invention described below, the capacitance measuring device is selected from the group consisting of a capacitance meter and a capacitance bridge.

According to still further features in the described preferred embodiments the capacitance measuring device is configured and designed to allow measuring of capacitance at a $1 \times 10^{-18}$ F resolution.

According to still further features in the described preferred embodiments the capacitance measuring device is operable to measure a time dependence of a change in capacitance.

According to still further features in the described preferred embodiments the particles arc dissolved in the fluid.

According to still further features in the described preferred embodiments the particles are dispersed in the fluid.

According to still further features in the described preferred embodiments the first and the second conductive plates are made of a material selected from the group consisting of Gold and Aluminium.

According to still further features in the described preferred embodiments the non conductive substrate is made of poly-Si.

According to still further features in the described preferred embodiments the method further comprising positioning the non conductive substrate onto a conductive substrate, prior to the step of etching.

According to still further features in the described preferred embodiments the conductive substrate is a doped Si wafer.

According to still further features in the described preferred embodiments the method further comprising grounding the conductive substrate.

According to still further features in the described preferred embodiments the step of providing the at least two electrical contacts is done by patterning and evaporation.

According to still further features in the described preferred embodiments the patterning is effected by at least one procedure selected from the group consisting of photolithography and lift-off technique.

According to still further features in the described preferred embodiments the electrical contacts comprise bonding pads.

According to still further features in the described preferred embodiments the method further comprising etching at least two reservoirs in the non conductive substrate prior to the stop of coating.

According to still further features in the described preferred embodiments the method further comprising covering the first and the second conductive plates by a non conductive slip having at least two holed so as to allow liquid passage therethrough into the at least two reservoirs.

According to still further features in the described preferred embodiments the conductive material is selected from the group consisting of Gold and Aluminium.

The present invention successfully addresses the shortcomings of the presently known configurations by providing a detector, for determining presence, number, length concentration, position and/or motion of at least one particle. The detector enjoys properties far exceeding those characterizing prior art detectors.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the, present invention only, and are presented in the cause of providing what is believed to be the most useful and readily understood description of the principles arid conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

The present invention is of a single molecule detector, a method of manufacturing same, and a method of detecting a single molecule which can be used for studying the behavior of single molecules. Specifically, the present invention can be used to determine a position and/or to monitor a velocity and acceleration of a single molecule, as well as to measure presence, number, length, or concentration of at least one particle such as a molecule.

The principles and operation of a single molecule detector according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Capacitance is a physical observable, attributed to a conductor or a system of conductors, which observable may be electrostatically defined as the ratio between a change in the electric charge on the conductor and the potential drop resulting from that change. The capacitance, C, of a capacitor depends on its geometry and on dielectric materials, if present which are adjacent to the conducting components of the capacitor. For example, for a parallel-plate capacitor the capacity is proportional to the area of the plates, and to the dielectric coefficient of the dielectric material (if present), and it is inversely proportional to the distance between the plates.

When a conductive particle having a non-negligible diameter compared to the distance between the plates of a parallel-plate capacitor, is placed within the inter-plate volume defined by the capacitor, the system experiences a change in the total capacitance, the amount of which is denoted herein by $\Delta C$ and is given by the formula:

$$\Delta C = \frac{1}{(d/\delta - 1)} \cdot \frac{\varepsilon A}{d}, \qquad \text{(Equation 1)}$$

where A is the area of each conductive plate, d is the distance between the plates and $\delta$ is the diameter of the conductive particle.

For capacitors in which d is large compared to $\delta$, the denominator of Equation 1 becomes large and this effect is negligible. However, a particle of the size of a single molecule may result in a detectable change of capacitance, if the distance between the plates is of the order of tens of nanometers. A detectable change of capacitance may be used for detecting the presence of the conductive particle.

Looking back at Equation 1, one recalls that the change in capacitance depends, not only on d, the width of the capacitor, but also on A, the area of the plates, as well as on ∈, the dielectric coefficient of the dielectric material, if present in the inter-plate volume.

While conceiving one aspect of the present invention and while reducing it to practice, it was uncovered that by appropriately varying at least one of the parameters d, A or ∈, the change in capacitance due to the presence of a conductive particle in the inter-plate volume becomes a function of a longitudinal position of the particle within the inter-plate volume. Such a capacitor can hence serve as a motion, e.g., velocity, acceleration, detector. Specifically, denoting the longitudinal position along a longitudinal axis of the inter-plate volume by Z, the most general embodiment of the present invention may be realized using the following formula:

$$\Delta C(Z) = \frac{1}{(d(Z)/\delta - 1)} \cdot \frac{\varepsilon(Z)A(Z)}{d(Z)}. \quad \text{(Equation 2)}$$

Hence, according to one aspect of the present invention, there is provided a detector for determining presence, number, length concentration, position and/or motion, e.g., acceleration and/or velocity of at least one particle, which detector is referred to herein as detector 10.

Figure 1:
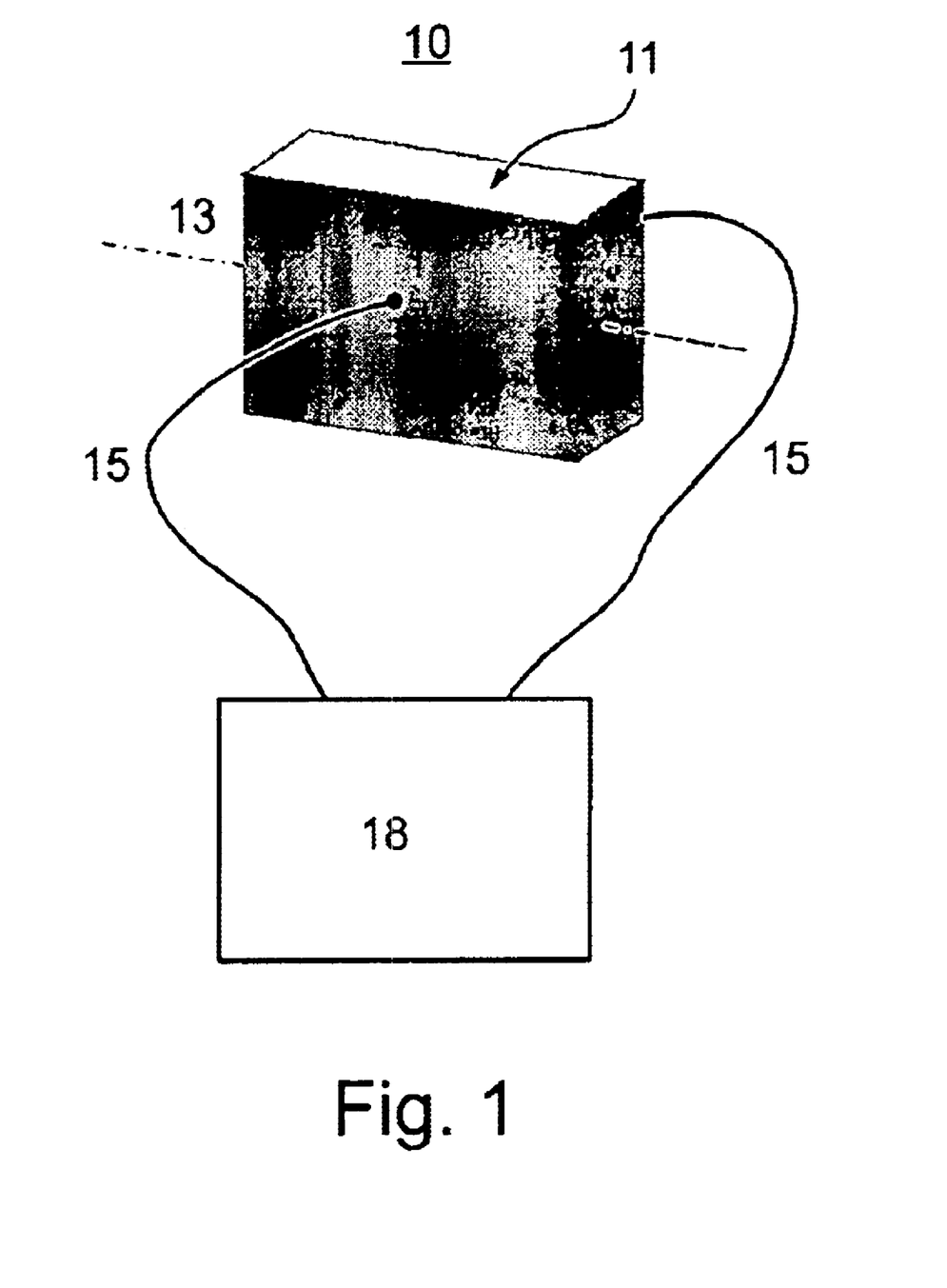
FIG. 1 is a detector according to the present invention.

Referring now to the drawings, FIG. 1 schematically illustrates detector 10, including, a capacitor 11, and at least two electrical contacts 15, connecting capacitor 11 to a capacitance measuring device 18.

Figure 2A:
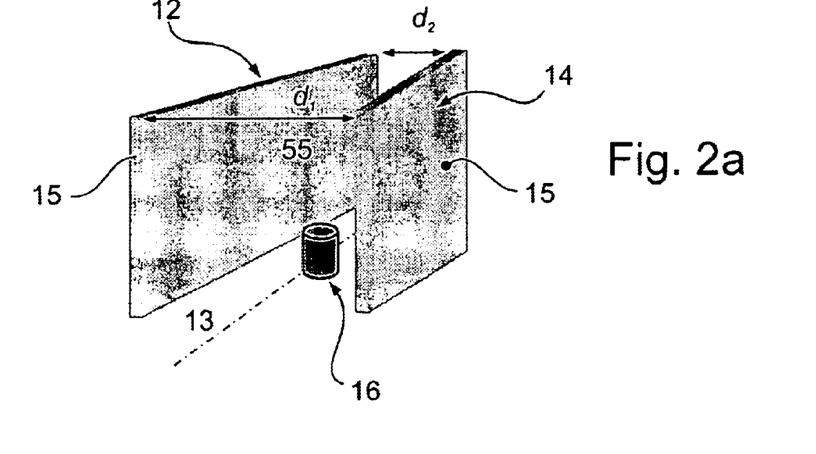
FIG. 2a is a variable-width capacitor according to the present invention.
Figure 2B:
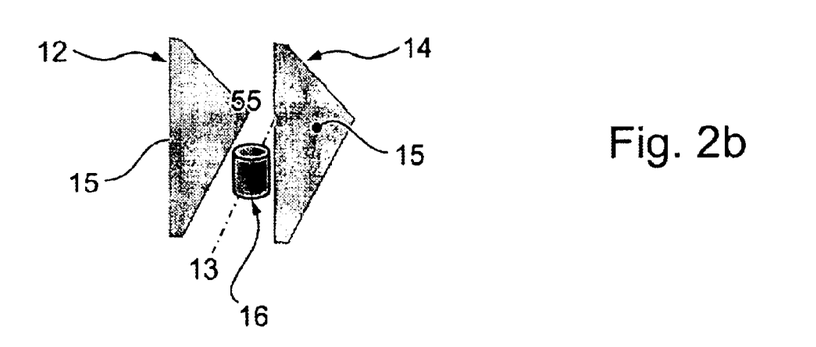
FIG. 2b is a capacitor having variable-area conductive plates according to the present invention.
Figure 2C:
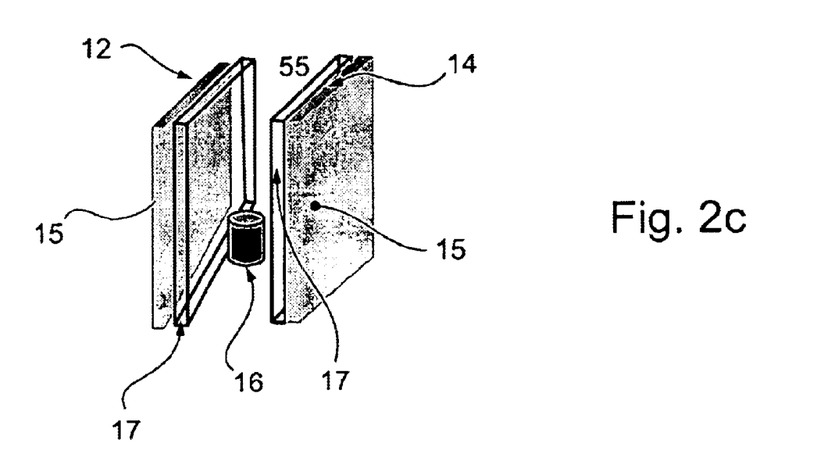
FIG. 2c is a capacitor having a variable dielectric coefficient according to the present invention.

Reference is now made to FIGS. 2a–c which schematically illustrate capacitor 11 in further detail. Capacitor 11 comprises a first conductive plate 12 and a second conductive plate 14, defining an inter-plate volume 55 having a longitudinal axis 13. According to a preferred embodiment of the present invention, capacitor 11 is characterized by at least one variable parameter, so as to allow monitoring a change of position of at least one charged particle 16, such as a single molecule, along longitudinal axis 13, which particle(s) 16 is placed within inter-plate volume 55 of capacitor 11, in a manner further described herein.

The at least one variable parameter may be a variable dielectric coefficient, a variable cross-sectional inter-plate volume, a variable plate width, and any possible combination thereof.

In one embodiment, shown in FIG. 2a, capacitor 11 is manufactured such that first conductive plate 12 and a second conductive plate 14 have a variable distance therebetween, hence defining inter-plate volume 55 of a variable-width. The variable distance between conductive plates 12 and 14 is materialized by positioning first conductive plate 12 and second conductive plate 14 is a substantially non-parallel orientation, hence allowing the distance between the plates to vary from a maximal distance (denoted $d_1$ in FIG. 2a) to a minimal distance (denoted $d_2$ in FIG. 2a). Hence, capacitor 11 is characterized by a variable cross section at any position along its longitudinal axis.

In another embodiment, shown in FIG. 2b, a transverse dimension of both first conductive plate 12 and second conductive plate 14 with respect to the longitudinal axis varies along the longitudinal axis. For example, as is specifically shown in FIG. 2b, first conductive plate 12 and second conductive plate 14 may each be manufactured having a triangular shape, thereby providing a different effective area A, at any position along the longitudinal axis. In other words, at each point along the longitudinal axis, a unique cross-sectional area of the inter-plate volume is defined.

In an additional embodiment, shown in FIG. 2c, dielectric material 17 may be inserted between first conductive plate 12 and second conductive plate 14. According to a presently preferred embodiment of the invention dielectric material 17 is manufactured with a dielectric coefficient, ∈, which vary as a function of the longitudinal position. Hence, the longitudinal position dependence of the change in capacitance, ΔC, is expressed through the longitudinal position dependence of ∈.

According to a preferred embodiment of the present invention, capacitance measuring device 18 may be any known device capable of measuring or determining capacitance, such as, but not limited to, a capacitance meter and a capacitance bridge. Capacitance measuring device 18 serves for detecting a change in the capacitance of capacitor 11, which change, in accordance with Equation 2, is a function of a longitudinal position of a charged particle placed in inter-plate volume 55. Hence, detector 10 of the present invention, allows, following, for example, the generation of a simple calibration curve, the determination of presence, number, length concentration, longitudinal position along longitudinal axis 13, or motion (e.g., velocity and/or acceleration) of at least one particle 16 placed within inter-plate volume 55 of capacitor 11. In order to determine motion parameters, capacitance measuring device 18 is selected operable to measure a time dependence of □C, thereby to measure a change in position of at least one particle 16, along longitudinal axis 13, so as to allow detector 10 to determine the position of particle(s) 16 as a function of time, which can be used to determine, via a simple mathematical transformation, particle's 16 velocity and/or acceleration within inter-plate volume 55.

The particles detected using detector 10 of the present invention may be for example cells, bacteria, biological molecules, organic molecules and polymers, provided these are characterized by a dielectric coefficient other than a dielectric coefficient of the medium engaging the inter-plate volume. Hence, according to a presently preferred embodiment of the invention, the particles are linked to at least one conductive particle, so as to promote the variation in dielectric coefficient of the system.

Figure 3:
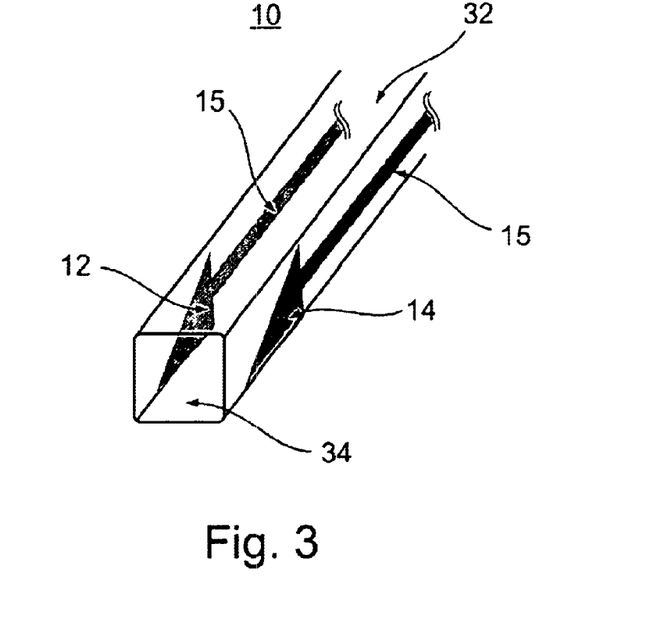
FIG. 3 is the detector, in which the conductive plates engage opposite outer-faces of a capillary, according to the present invention.

Reference is now made to FIG. 3, illustrating a certain configuration of detector 10, in which according to a presently preferred embodiment of the invention, first 12 and second 14 conductive plates engage opposite outer-faces of a capillary 32 having a square profile 34. It would be appreciated that profile 34 may have any other shape, such as but not limited to, a polygonal profile (other than a square), a circular profile an ellipsoidal profile and an irregular pattern profile. According to this embodiment, capacitor 11 is constructed as a parallel-plate capacitor in which the area A of first conductive plate 12 and second conductive plate 14 is a function of Z, however, the capillary structure of detector 10, may be employed with any of the above embodiments.

For example, as is further detailed hereinunder, a variable distance between the plates may be achieved by using a capillary manufactured in a manner that its diameter gradually decreases along it's longitudinal axis. Those skilled in the art would appreciate that such capillaries are characterized by a variable cross section at any position along the longitudinal axis.

Figure 4:
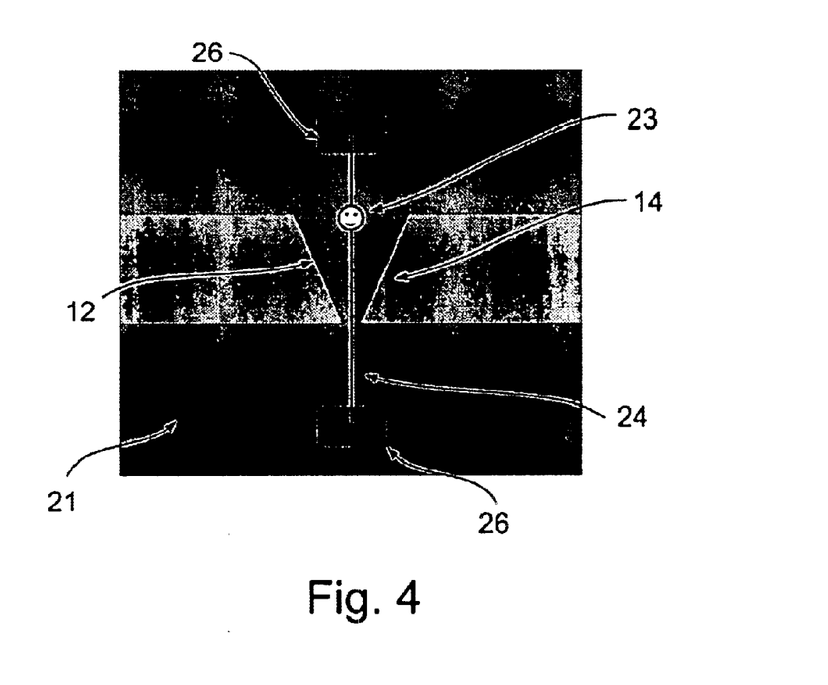
FIG. 4 is a top view of the detector fabricated using planar geometry according to the present invention.

Reference is now made to FIG. 4, showing a top view of planar geometry which may be employed to fabricate a detector 10 according to the present invention. First conductive plate 12 and second conductive plate 14 are defined using two metal electrodes, fabricated on a Si substrate 21. As will be appreciated by one ordinarily skilled in the art, this may be achieved using any constructive and/or destructive technique known in the field of electronic microfabrication, such as, but not limited to, evaporation, lithography and/or lift-off techniques.

The capacitor shown in FIG. 4 can be used, for example, for monitoring the motion of a molecular motor 23 bound to, and migrating along, a DNA molecule 24 which is connected at each end thereof to a respective Gold plate 26, positioned outside inter-plate volume 55 of capacitor 11. For such use, first conductive plate 12 and second conductive plate 14 are fabricated from a conductive material other than Gold (e.g. Aluminium), so as to prevent attachment of DNA molecule 24 to the plates. The DNA molecule may be modified to include an SH group at its ends, so as to facilitate covalent binding to Gold plates 26.

It will be appreciated that detector 10 can also be used to monitor motion in other applications. For example, detector 10 can be used for studying macromolecular transport through gated channels, where currently no such data are available, or for direct monitoring of a single sperm cell motion without requiring complex mathematical image and/ or signal analysis. In addition, detector 10 may be used to study flow through extremely small vessels, by tagging liquids with conductive particles. Still in addition, detector 10 of the present invention can be advantageously used in the inkjet industry, where the velocity and/or quantity of ink drops are to be monitored once leaving the "print head".

Equation 1, which is the degenerate case of Equation 2, where all parameters are constant is also of interest with respect to another aspect of the present invention.

Figure 5:
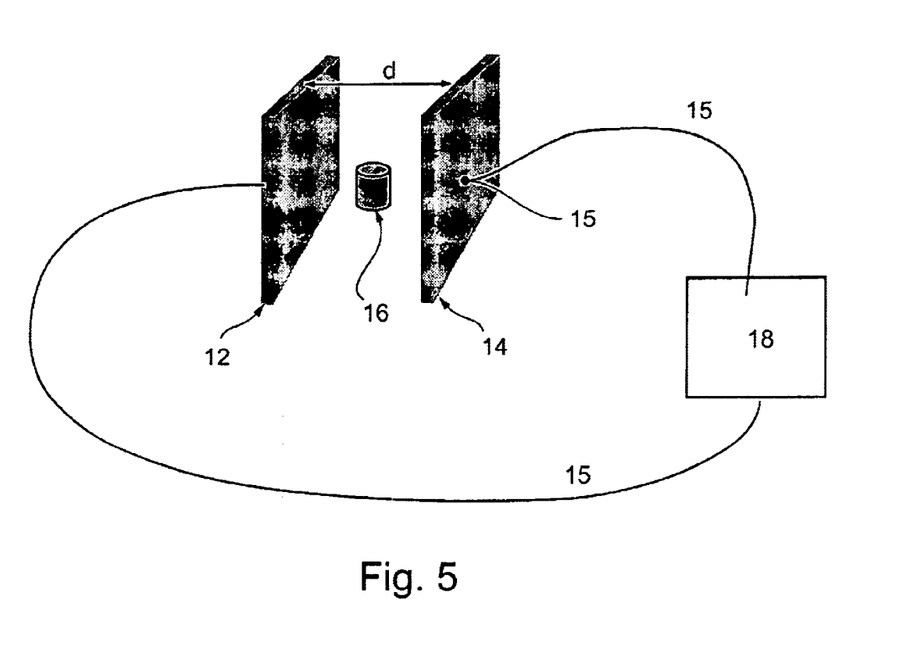
FIG. 5 is a detector comprising a parallel-plate capacitor according to the present invention.

Referring now to FIG. 5, according to another aspect of the present invention there is provided a particles presence, number, length or concentration detector, which is referred to herein as detector 20. Detector 20 includes capacitor 11 which comprises first conductive plate 12 and second conductive plate 14, which is substantially parallel to first conductive plate 12. First conductive plate 12 and second conductive plate 14 define an inter-plate volume having a longitudinal axis. Detector 20 further includes at least two electrical contacts 15, connecting each of first 12 and second 14 conductive plates to a capacitance measuring device 18.

As for detector 10, capacitance measuring device 18 serves for detecting a change in the capacitance of capacitor 11, which change, in accordance with Equation 1, allows, following, for example, the generation of a simple calibration curve, the determination of presence, number, length and concentration of at least one conductive particle 16. The detected particles may be for example cells, bacteria, biological molecules, organic molecules and polymers, provided these are inherently charged or modified to be charged. Hence, according to a presently preferred embodiment of the invention, the particles are linked to at least one conductive particle, so as to promote the conductivity of the system.

A skilled artisan would appreciate that the functionality of detector 20 is basically binary, in a sense that it detects the presence of conductive particle 16 in detector 20, whereas the position and/or change of position of conductive particle 16 is not recorded via detector 20.

Hence, detector 20 can be used for the detection and dielectric characterization of single molecules which are placed in the inter-plate volume. This type of detection scheme is ideally suited for automated medical laboratory testing. For example, the direct relation between the number of particles, within the capacitor plates and the detected capacitance can be used for determining the number or concentration of particles. It may be possible to distinguish between molecules based on the difference in their dielectric constant which affect the value of $\Delta C$. In addition, a time dependent profile of $\Delta C$ can be used to measure the length of polymer chains, both synthetic and biological (e,g. a DNA), once such polymer is made to flow through detector 20.

According to any embodiment of the present invention the distance between first conductive plate 12 and second conductive plate 14 at any position along the longitudinal axis of the interplate volume may be at any scale, such as but not limited to a nanometer scale. In the case of narrowing inter-plate volume distances varying from about 100 to about 10 nm for example, can be employed, so as to allow detection at a nanometer resolution. Such width selection ensures that detectors 10 and 20 would be operable at a nanometer resolution, as the ratio $d/\delta$ (Equation 1) would be, in terms of order of magnitude, comparable to unity. As is further exemplified in the Examples section below, simulations show that the values of $\Delta C$ obtained for the above sub-microns width, are in a capacitance region of $10^{-17}$ F. Hence, according to a preferred embodiment of the present invention, capacitance measuring device 18 is configured and designed to allow measuring of capacitance at a $1 \times 10^{-18}$ F resolution. In addition, the time resolution of detectors 10, and 20, which depends inter-alia on the quality of capacitance measuring device 18, is in a sub-microsecond time scales.

Another aspect of the present invention relates to method of manufacturing detectors 10 and/or 20, which methods are further described herein under.

In a method of manufacturing a detector for detecting at least one conductive particle a first conductive plate and a second conductive plate are positioned in a manner such that second conductive plate is spaced apart from first conductive plate, so as to define an inter-plate volume having longitudinal axis. A second step of the method comprises providing at least two electrical contacts connecting each of the first and second conductive plates to a capacitance measuring device. As stated, the capacitance measuring device may be any know device capable of measuring or determining capacitance, such as, but not limited to, a capacitance meter and a capacitance bridge.

In a preferred embodiment in which a dielectric material is employed, the method may further comprise providing the dielectric material between the first and second conductive plates. The dielectric material may be characterized by either a constant dielectric coefficient or by a dielectric coefficient which varies along the longitudinal axis.

Figure 6:
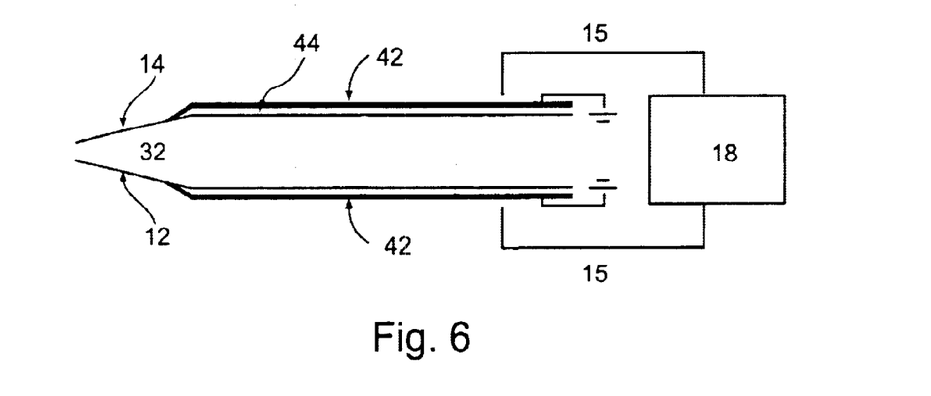
FIG. 6 is a detailed illustration of the manufacturing method of the detector in a capillary structure, according to the present invention.

Reference is now made to FIG. 6, illustrating a motion detector manufactured according to the one embodiment of the present invention. In this embodiment, positioning the first conductive plate and the second conductive plate is preceded by providing a pullable tube having a profile, and pulling the tube at a controlled rate so as to provide a capillary 32, having a predetermined maximal diameter.

A suitable tube may be for example, a commercial 1 mm×0.5 mm quartz pipette. The step of pulling the tube so as to generate a capillary may be preformed using any known technique conventionally employed for capillary generation, e.g., using a $CO_2$ laser based micropipette puller. The pulling conditions, i.e., laser intensity, and force of the pull tune the exact geometry of the formed capillary. For example, in a preferred embodiment in which a variable-width capacitor is employed, the pulling conditions are designed so as to produce tapered ends (see FIG. 6).

Once capillary 32 is provided, first conductive plate 12 and second conductive plate 14 are applied onto capillary 32. This may be done either onto opposite inner-faces or onto opposite outer-faces of capillary 32. In addition, first conducive plate 12 and second conductive plate 14 may be applied either directly on capillary 32 or onto at least one intermediate layer, as described herein.

Thus, according to a presently preferred embodiment of the invention, the method further comprising applying at least one additional conductive layer 42 onto capillary 32, and covering conductive layer 42 by an electrical isolating layer 44, prior to the step of applying first 12 and second 14 conductive plates. Layer 42 is preferably grounded so as to reduce an effect of parasitic capacitance on the non-active part of capillary 32. Layer 42 may be made of any conductive material, such as, but not limited to, Gold or Aluminum. Electrical isolating layer 44 may be made from any non-conductive material, such as, but not limited, to quartz. All the formed layers and plates may be applied using any technique know in the art such as evaporation, lift-off, shadow-evaporation, nano-manipulation and focused ion milling, using e.g., atomic force microscope.

Figure 7:
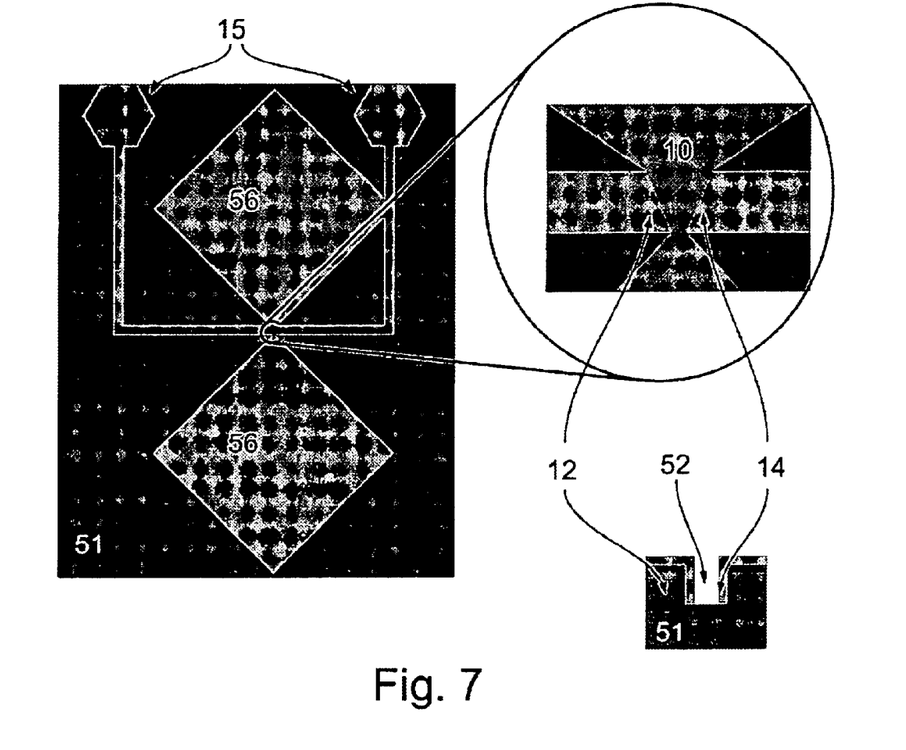
FIG. 7 is a is a detailed illustration of the manufacturing method of the detector in a planar structure, according to the present invention.

Reference is now made to FIG. 7, which depicts a planar configuration of detector 10, according to a preferred embodiment of the present invention. A method for manufacturing a motion detector, based on planar geometry is herein described.

Hence, according to this embodiment of the present invention there is provided a method of manufacturing a motion detector for detecting at least one conductive particle, the method comprising the following manufacturing steps. In a first step a non conductive substrate 51 is etched, so as to provide a channel 52 having walls. In a second step, follow the etching, the walls of the channel are coated by a conductive material, so as to form first conductive plate 12 and a second conductive plate 14. A side view of the coated walls forming first 12 and second 14 conductive plate are shown in the lower right corner of FIG. 7. In a third step, at least two electrical contacts 15, are applied, e.g. by patterning and evaporation of a conductive material, onto non conductive substrate 51. Electrical contacts 15 serve for connecting each of first 12 and second 14 conductive plates to a capacitance measuring device (not shown in the Figure).

According to a preferred embodiment of the invention, the method may further comprise etching at least two reservoirs 56 in non conductive substrate 51. Reservoirs 56 serve for allowing interface of a liquid handling system to the detector. In addition, an optional step of covering first 12 and second 14 conductive plates by a non conductive slip may also be employed. Such a non-conductive slip, which serves as a protector of the detector, may include at least two holes such that the holes are positioned above reservoirs 56 so as to allow liquid containing the molecules or particles of choice to be injected into the device.

According to the present invention the non conductive substrate employed is, for example, a poly-Si layer which is preferably deposited over a heavily doped Si wafer which, in addition to providing a base for the device, forms a ground plane shield. The pattering may comprise any constructive and/or destructive procedure known in the field of electronic microfabrication, for example, photolithography and lift-off techniques.

First conductive plate 12 and second conductive plate 14, as well as electrical contacts 15, may be made of any conductive material such as, but not limited to, Gold and Aluminium.

According to a preferred embodiment of the present invention, detectors 10, and/or 20 may be placed in a shielded, low-noise, enclosure so as to minimize the influence of external noise sources. The enclosure also serves as a temperature-stabilized environment and as a vibration isolator. Those skilled in the art would appreciate that the electronic noise resulting from any measurement system is negligible even for commercially available components. To further reduce error associated with drifts, a second capacitor, connected in parallel with capacitor 11, may be used as the reference arm of the capacitance bridge. The second capacitor effectively eliminates drifts resulting from temperature, humidity and pressure variations in the enclosure.

Capacitive detectors are renowned for their stability, sensitivity and their high degree of immunity to external interference. Using the concept capacitive detection, the present invention offers the possibility of obtaining meaningful information on previously unattainable length scales.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Example 1

The ultimate spatial resolution of the detector of the present invention is determined by the ability to measure very small changes in capacitance. To estimate the required sensitivity, and with typical dimensions of relevant biological systems in mind, simulations on a 100 nm-long capacitor whose width varies from 40 to 60 was performed with respect to a 35×35×35 nm$^3$ conducting cube placed in the inter-plate volume.

Figure 8:
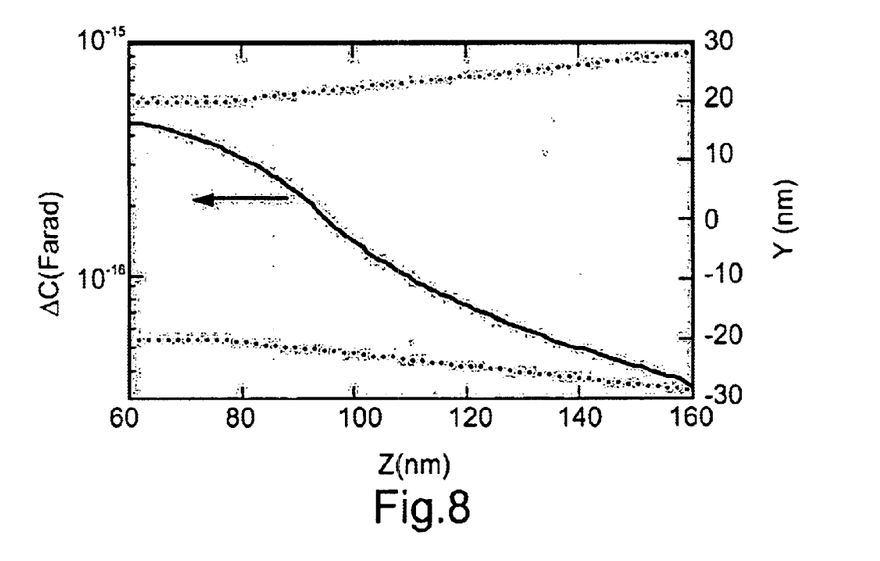
FIG. 8 is a graph of the change in capacitance measured in Farads, as a function of the longitudinal position, measured in nanometers.

Reference is now made to FIG. 8, showing a graph of the change in capacitance $\Delta C$, measured in Farads, as a function of the longitudinal position Z, measured in nanometers. The dotted line in the graph illustrates the distance between the plates, as marked on the right hand side of FIG. 5 (the distance is denoted Y on the graph). The solid line shows the results of the simulation. As can be inferred from FIG. 8, by moving in a direction indicated by the arrow, the conducting cube induced a capacitance change ranging from $1\times10^{-17}$ F to $1\times10^{-15}$ F, which range is within the technological capability of commercially available capacitance measuring devices, capable of measuring capacitance as low as $1\times10^{-18}$ F. Hence the resolution of the detector is demonstrated herein to be of about 1 nanometer.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A detector, for determining presence, number, length, concentration, position and/or motion of at least one particle present in a fluid and having a dielectric coefficient other than a dielectric coefficient of the fluid, the detector comprising:

(a) a capacitor, comprising a first conductive plate and a second conductive plate defining an inter-plate volume having a longitudinal axis; and (b) at least two electrical contacts, connecting each of said first and second conductive plates to a capacitance measuring device;

said capacitor being characterized by at least one variable parameter so as to allow determination and/or monitoring of presence, number or concentration of the at least one particle, and at least one additional quantity of the at least one particle, said at least one additional quantity being selected from the group consisting of length, position and at least one motion characteristic of the at least one particle placed within said inter-plate volume of said capacitor.

2. The detector of claim 1, wherein the at least one particle is dissolved in the fluid.

3. The detector of claim 1, wherein the at least one particle is dispersed in the fluid.

4. The detector of claim 1, wherein said capacitance measuring device is selected from the group consisting of a capacitance meter and a capacitance bridge.

5. The detector of claim 1, wherein said at least one variable parameter is selected from the group consisting of a variable dielectric coefficient and a variable cross-sectional area, said cross-sectional area being perpendicular to said longitudinal axis.

6. The detector of claim 1, wherein at least one of the at least one particle is self-conductive.

7. The detector of claim 1, wherein at least one of the at least one particle is linkable to at least one conductive particle.

8. The detector of claim 1, wherein the at least one particle is selected from the group consisting of a cell, a bacterium, a biological molecule, an organic molecule and a polymer.

9. The detector of claim 1, wherein said determination and/or monitoring is at a nanometer resolution.

10. The detector of claim 1, wherein said capacitance measuring device is configured and designed to allow measuring of capacitance at a $1 \times 10^{-18}$ F resolution.

11. The detector of claim 1, wherein said determination and/or monitoring is in a sub-microsecond time scales.

12. The detector of claim 1, wherein said capacitance measuring device is, operable to measure a time dependence of a change in capacitance.

13. The detector of claim 1, wherein said first and second conductive plates engage opposite inner-faces of a capillary.

14. The detector of claim 1, wherein said first and second conductive plates engage opposite outer-faces of a capillary.

15. The detector of claim 1, wherein said capillary has a profile selected from the group consisting of a polygonal profile a circular profile an ellipsoidal profile and an irregular pattern profile.

16. The detector of claim 13, wherein said capillary is characterized by a variable cross section at any position along said longitudinal axis.

17. The detector of claim 1, wherein a transverse dimension of said first and said second conductive plates, with respect to said longitudinal axis, is constant along said longitudinal axis.

18. The detector of claim 1, wherein a transverse dimension of said first and said second conductive plates, with respect to said longitudinal axis varies along said longitudinal axis.

19. The detector of claim 1, wherein said at least one motion characteristic is selected from the group consisting of a velocity and an acceleration.

20. The detector of claim 1, further comprising at least one additional conductive layer interposted between said first and said second conductive layers, said at least one additional conductive layer having a surface area substantially smaller than a surface area of both said first and said second conductive layers.

21. The detector of claim 20, further comprising at least one electrical isolating layer, covering said at least one additional conductive layer.

22. The detector of claim 20, wherein at least one additional conductive layer is grounded.

23. The detector of claim 20, wherein said at least one additional conductive layer is a made of Gold.

24. The detector of claim 21, wherein said electrical isolating layer is a made of quartz.

25. The detector of claim 1, wherein said first and said second conductive plates are made of a material selected from the group consisting of Gold and Aluminium.

26. A motion detection method comprising placing at least one particle, present in a fluid and having a dielectric coefficient other than a dielectric coefficient of the fluid, within an inter-plate volume of a capacitor being characterized by at least one variable parameter, and determining and/or monitoring presence, number or concentration of the at least one particle, and at least one additional quantity of the at least one particle, said at least one additional quantity being selected from the group consisting of length, longitudinal position and at least one motion characteristic of said at least one particle, by determining a change in capacitance of said capacitor.

27. The motion detection method of claim 26, wherein the at least one particle is dissolved in the fluid.

28. The motion detection method of claim 26, wherein the at least one particle is dispersed in the fluid.

29. The motion detection method of claim 26, wherein said change in capacitance comprises time dependent change in capacitance.

30. The motion detection method of claim 26, wherein at least one of said at least one variable parameter is selected from the group consisting of a variable dielectric coefficient and a variable cross-sectional area, said cross-sectional area being perpendicular to a longitudinal axis defined in an inter-plate volume of said capacitor.

31. The motion detection method of claim 26, wherein each of said at least one particle is linkable to a particle selected from the group consisting of a cell, a bacterium, a biological molecule, an organic molecule and a polymer.

32. The motion detection method of claim 26, wherein said determining is at a nanometer resolution.

33. The motion detection method of claim 26, wherein said monitoring is at a sub-microsecond time scales.

34. The motion detection method of claim 26, wherein said at least one motion characteristic is selected from the group consisting of a velocity and an acceleration.

35. A particle presence, number, length or concentration detector comprising:
(a) a capacitor, comprising a first conductive plate and a second conductive plate substantially parallel to said first conductive plate, said first and second conductive plates defining an inter-plate volume having a longitudinal axis; and
(b) at least two electrical contacts, connecting each of said first and second conductive plates to a capacitance measuring device;
said capacitor being designed and constructed for allowing a determination of a presence, number or concentration of particles placed within said inter-plate volume of said capacitor, and at least one additional quantity of said particles;
wherein said particles are present in a fluid and having a dielectric coefficient other than a dielectric coefficient of said fluid, and further wherein said at least one additional quantity is selected from the group consisting of length, position and at least one motion characteristic of said particles.

36. The particles presence, number, length or concentration detector of claim 35, wherein said particles are dissolved in the fluid.

37. The particles presence, number, length or concentration detector of claim 35, wherein said particles are dispersed in the fluid.

38. The particles presence, number, length or concentration detector of claim 35, wherein said capacitance measuring device is selected from the group consisting of a capacitance meter and a capacitance bridge.

39. The particles presence, number, length or concentration detector of claim 35, wherein said particles are selected from the group consisting of cells, bacteria, biological molecules, organic molecules and polymers.

40. The particles presence, number, length or concentration detector of claim 35, wherein each of said particles are linkable to at least one conductive particle.

41. The particles presence, number, length or concentration detector of claim 35, wherein said particles are self-conductive.

42. The particles presence, number, length or concentration detector of claim 35, wherein said determination is at a nanometer resolution.

43. The particles presence, number, length or concentration detector of claim 35, wherein said capacitance measuring device is configured and designed to allow measuring of capacitance at a $1 \times 10^{-18}$ F resolution.

44. The particles presence, number, length or concentration detector of claim 35, wherein said first and second conductive plates engage opposite inner-faces of a capillary.

45. The particles presence, number, length or concentration detector of claim 35, wherein said first and second conductive plates engage opposite outer-faces of a capillary.

46. The particles presence, number, length or concentration detector of claim 44, wherein said capillary has a profile selected from the group consisting of a polygonal profile a circular profile an ellipsoidal profile and an irregular pattern profile.

47. The particles presence, number, length or concentration detector of claim 35, wherein said first and said second conductive plates are made of a material selected from the group consisting of Gold and Aluminium.

48. A method of determining the presence, number, length or concentration of particles present in a fluid and having a dielectric coefficient other than a dielectric coefficient of the fluid, the method comprising placing the particles and the fluid in an inter-plate volume of a parallel plates capacitor and determining the presence, number or concentration of the particles, and at least one additional quantity of the particles, by determining a change in capacitance of said parallel plates capacitor;
wherein said at least one additional quantity is selected from the group consisting of length, position and at least one motion characteristic of the particles.

49. The method of claim 48, wherein said particles are dissolved in the fluid.

50. The method of claim 48, wherein said particles are dispersed in the fluid.

51. The method of claim 48, wherein said particles are selected from the group consisting of a cell, a bacterium, a biological molecule, an organic molecule and a polymer.

52. The method of claim 48, wherein each of said particles is linkable to at least one conductive particle.

53. The method of claim 48, wherein said particles comprise self-conductive particles.

54. The method of claim 48, wherein said determining is at a nanometer resolution.

* * * * *